United States Patent
Hill et al.

(10) Patent No.: US 9,265,678 B2
(45) Date of Patent: Feb. 23, 2016

(54) MODULAR PATIENT CARE ENCLOSURE

(71) Applicant: AMERICAN STERILIZER COMPANY, Mentor, OH (US)

(72) Inventors: Aaron Leif Hill, Madison, OH (US); Thaddeus Joseph Mielnik, Concord, OH (US); Ryan Anthony Bruskevith, Mentor, OH (US)

(73) Assignee: American Sterilizer Company, Mentor, OH (US)

( * ) Notice: Subject to any disclaimer, the term of this patent is extended or adjusted under 35 U.S.C. 154(b) by 295 days.

(21) Appl. No.: 13/944,957

(22) Filed: Jul. 18, 2013

(65) Prior Publication Data

US 2015/0025300 A1    Jan. 22, 2015

(51) Int. Cl.
*A61G 10/00* (2006.01)
*A61G 10/02* (2006.01)
(Continued)

(52) U.S. Cl.
CPC ............ *A61G 10/005* (2013.01); *A61G 10/023* (2013.01); *A61L 2/10* (2013.01); *A61L 9/16* (2013.01); *A61L 9/20* (2013.01);
(Continued)

(58) Field of Classification Search
CPC .............. A61G 10/005; A61G 10/023; A61G 11/00–11/009; A61G 10/00–10/009; A61L 2202/14; A61L 2202/25; A61L 2209/111; A61L 2209/14; A61L 2209/16; A61L 2209/212; A61L 2/10; A61L 9/16; A61L 9/20; A61L 9/22; F24F 3/16–3/161; F24F 2007/004; F24F 13/06; B08B 15/023
USPC ............................................. 600/21; 454/238
See application file for complete search history.

(56) References Cited

U.S. PATENT DOCUMENTS 2,482,341 A * 9/1949 Holmsten .................. E05C 1/04
292/148
4,129,122 A * 12/1978 Dout ...................... A61G 10/02
454/188

(Continued)

FOREIGN PATENT DOCUMENTS

GB          2050841 A  *  1/1981

OTHER PUBLICATIONS

Sun Porch. "Sunrooms, Three Season Rooms, Solariums, Screen Rooms & Patio Rooms, Patio Enclosures, Sun Porch and Screen Porch Sizes, Models & Prices." Web. Jun. 26, 2015. <https://web.archive.org/web/20050306085121/http://www.sunporch.com/>. PDF attached.*

(Continued)

*Primary Examiner* — Charles A Marmor, II
*Assistant Examiner* — Lauren Querido
(74) *Attorney, Agent, or Firm* — Kusner & Jaffe; Michael A. Centanni (57) ABSTRACT

A patient enclosure, comprised of at least two spaced-apart side walls, a top wall, and a front wall, the side walls, the top wall, and the front wall defining a predetermined area surrounding a location where a patient is positionable. At least one of the walls has a panel of electrochromic glass that is switchable between a clear state, an opaque state and a reflective (mirrored) state. UV radiators are provided within the area of the enclosure. An air circulation system is provided for circulating air through the area defined by the enclosure. A controller controls the UV radiators and the air circulation system. The controller is programmed to create one of a higher pressure or a lower pressure within the area as compared to the environment surrounding the enclosure.

18 Claims, 5 Drawing Sheets

(51) Int. Cl.
*A61L 9/16* (2006.01)
*A61L 9/20* (2006.01)
*A61L 2/10* (2006.01)
*A61L 9/22* (2006.01)

(52) U.S. Cl.
CPC .............. *A61L 9/22* (2013.01); *A61L 2202/14* (2013.01); *A61L 2202/24* (2013.01); *A61L 2202/25* (2013.01); *A61L 2202/26* (2013.01); *A61L 2209/111* (2013.01); *A61L 2209/14* (2013.01); *A61L 2209/16* (2013.01); *A61L 2209/212* (2013.01)

(56) References Cited

U.S. PATENT DOCUMENTS

| | | | | |
|---|---|---|---|---|
| 5,074,894 A | | 12/1991 | Nelson | 55/210 |
| 5,472,466 A | * | 12/1995 | Oler | F24F 7/013 454/253 |
| 5,905,590 A | * | 5/1999 | Van Der Sluis et al. | 359/275 |
| 6,811,748 B2 | * | 11/2004 | Ettlinger | A61L 2/10 250/455.11 |
| 7,189,349 B2 | | 3/2007 | Karle | 422/28 |
| 8,067,750 B2 | * | 11/2011 | Deal | 250/455.11 |
| 8,216,523 B2 | | 7/2012 | Meilander et al. | 422/294 |
| 2005/0129571 A1 | * | 6/2005 | Centanni | 422/31 |
| 2007/0098592 A1 | | 5/2007 | Buczynski et al. | 422/3 |
| 2007/0113842 A1 | | 5/2007 | Glazman | 128/200.15 |
| 2007/0184769 A1 | * | 8/2007 | Lin | 454/57 |
| 2010/0047116 A1 | | 2/2010 | Garner | 422/4 |
| 2010/0182674 A1 | * | 7/2010 | Nichols | 359/275 |
| 2010/0266445 A1 | * | 10/2010 | Campagna | A61L 2/10 422/23 |
| 2011/0079732 A1 | * | 4/2011 | Kreitenberg | A61L 2/10 250/455.11 |
| 2012/0285459 A1 | | 11/2012 | Sata et al. | 128/205.12 |
| 2013/0216438 A1 | * | 8/2013 | Hill et al. | 422/119 |

OTHER PUBLICATIONS

Sound Seal. "Portable Acoustical Enclosures & Screens" N.p., n.d. Web. Jun. 26, 2015. <http://www.soundseal.com/pdfs/ss-103-72res.pdf>. PDF attached.*

U.S. Appl. No. 13/764,814 entitled: Vaporized Hydrogen Peroxide Decontamination Structure to Aaron Leif Hill et al., filed Feb. 12, 2013.

* cited by examiner

MODULAR PATIENT CARE ENCLOSURE

FIELD OF THE INVENTION

The present invention relates generally to patient care facilities within a hospital/clinical facility and, more specifically, to a self-contained patient enclosure within a hospital/clinical facility.

BACKGROUND OF THE INVENTION

A major concern of medical facilities, namely, hospitals and clinics, is the transmission of harmful organisms and bacteria within the facility. In this respect, hospital environments are known to contain organisms, such as Methicillin-resistant *Staphylococcus aureus* (MRSA) and *Clostridium difficile* (*C. Diff*), that are known to be resistant to currently available antibiotics. These organisms are particularly troublesome in hospitals because patients with open wounds, invasive devices, and weakened immune systems are at greater risk of infection than the general public. With the significant interaction between patients and medical staff, as well as patients, family members, and visitors, reduction of hospital-acquired infections is particularly important.

Because the foregoing organisms are generally resistant to currently available antibiotics and can exist on surfaces within a room, including furniture, hospital bedding and medical equipment, infected patients are often isolated from other patients within the medical facility, and rooms and equipment are cleaned following release of the patient.

One current method of killing organisms within a room involves the use of vaporized hydrogen peroxide. Because of the hazardous nature of vaporized hydrogen peroxide, the patient care room or patient isolation room must be made leak-tight to insure that hydrogen peroxide gas remains within the room and levels of hydrogen peroxide outside the room do not exceed one part per million (ppm). Another problem with using vaporized hydrogen peroxide is that a vaporized-hydrogen-peroxide sterilization cycle typically takes upwards of two to three hours to complete, including a lengthy aeration phase to break down the vaporized hydrogen peroxide to safe levels. Moreover, the risk of hydrogen peroxide leaking into adjacent areas of the medical facility through the HVAC system is a significant concern. Even when a room is sterilized using vaporized hydrogen peroxide, once the room is open, airborne organisms and bacteria can enter the room as a result of normal circulation of air in the medical facility. In this respect, in some instances, it is necessary to protect patients (such as burn victims) who are highly susceptible to airborne bacteria and organisms from being exposed to bacteria, organisms, and viruses in the atmosphere typically found in the hospital environment.

The present invention overcomes these and other problems and provides a patient enclosure that can be quickly decontaminated using UV radiation and that can control the atmosphere within the enclosure to confine the atmosphere within the enclosure from migrating out of the enclosure or can maintain the environment atmosphere outside the enclosure from entering the enclosure.

SUMMARY OF THE INVENTION

In accordance with a preferred embodiment of the present invention, there is provided a patient enclosure, comprised of at least two spaced-apart side walls, a top wall, and a front wall. The side walls, the top wall, and the front wall together define a predetermined area surrounding a location where a patient is positionable. At least one of the walls has a panel of electrochromic glass that is switchable between a clear, transparent state, an opaque state and a light reflective (mirror) state. An opening is provided through one of the walls allowing access into the area. A door is provided within the opening. The door is movable between an open position allowing access to the area and a closed position preventing access to the area. UV radiators are provided within the area of the enclosure. An air circulation system circulates air through the area defined by the enclosure. The air circulation system is comprised of a conduit having distal ends communicating with the area within the enclosure at spaced-apart locations in the enclosure, and a blower for blowing air through the enclosure. An air filtration system is connected to the conduit such that air flowing through the conduit is filtered by the air filtration system. An air inlet connects the area within the enclosure with the environment surrounding the enclosure. The air inlet has an inlet valve controlling air flow therethrough. An air outlet connects the area within the enclosure with the environment surrounding the enclosure. The air outlet has an outlet valve controlling air flow therethrough. A controller controls the UV radiators, the blower, the inlet valve, and the outlet valve. The controller is programmed to create one of a higher pressure or a lower pressure within the area as compared to the environment surrounding the enclosure.

An advantage of the present invention is a patient enclosure that contains a hospital bed and necessary furniture and medical equipment required for proper patient care, which room can be decontaminated using UV radiation.

Another advantage of the present invention is an enclosure as described above that does not require the enclosure to be sealed (airtight) from the surrounding environment.

Another advantage of the present invention is an enclosure as described above wherein the atmosphere within the enclosure can be controlled to prevent airborne organisms within the atmosphere of the enclosure from exiting the enclosure.

A still further advantage of the present invention is an enclosure as described above wherein the environment within the enclosure can be controlled such that airborne viruses and organisms outside the enclosure can be prevented from entering the enclosure.

A still further advantage of the present invention is an enclosure as described above wherein UV radiators are permanently mounted within the enclosure and are operable when energized to kill harmful organisms, bacteria, and viruses within the enclosure.

A still further advantage of the present invention is an enclosure as described above having window panels that have variable light-transmissive properties depending upon a voltage applied to the panels.

A still further advantage of the present invention is an enclosure as described above having an air filtration system operable to control the pressure within the enclosure.

Another advantage of the present invention is an enclosure as described above wherein the air filtration system includes a plasma generator which generates an oxidative species operable to kill bacteria in the air that is circulated through the enclosure.

Another advantage of the present invention is an enclosure as described above wherein the air filtration system includes a catalytic converter for destroying any ozone circulating through the circulation system that may be introduced into the enclosure.

A still further advantage of the present invention is a controller for controlling the pressure within the enclosure wherein a pressure higher than that of the environment surrounding the enclosure can be established within the enclosure to prevent air from outside the enclosure from entering into the enclosure.

Another advantage of the present invention is an enclosure as described above wherein the pressure within the enclosure can be maintained at a pressure less than the pressure of the environment surrounding the enclosure to maintain the environment within the enclosure from being released to the environment surrounding the enclosure.

Another advantage of the present invention is an enclosure as described above that can be assembled within an existing room within a medical facility.

A still further advantage of the present invention is an enclosure as described above that includes a thermal detector or a motion detector that insures that no person is within the enclosure when UV radiators are activated to kill viruses and other biocontamination within the enclosure.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Referring now to the drawings wherein the showings are for the purpose of illustrating a preferred embodiment of the invention only and not for the purpose of limiting same, the drawings show an enclosure 10, illustrating a preferred embodiment of the present invention. In the embodiment shown, enclosure 10 is comprised of two spaced-apart side walls 22, 24, a top wall 26, and a front wall 28. Enclosure 10 is shown positioned on a floor 12 and against a vertical wall 14 of an existing structure. In this respect, floor 12 of the existing structure essentially defines a bottom wall of enclosure 10, and vertical wall 14 of the existing structure defines a back wall of enclosure 10.

Enclosure 10 is dimensioned to define an area surrounding a location where a patient is positionable. In the embodiment shown, a patient care location is defined by a hospital bed 32, a stand 34 adjacent bed 32, a portable table 36 for use in conjunction with hospital bed 32, and a medical panel 38 mounted to vertical wall 14 of the existing structure.

In the embodiment shown, side walls 22, 24 are essentially identical. Each is comprised of a generally rectangular frame 42 having spaced-apart vertical dividers 44. Frame 42 and dividers 44 define four like regions or zones that hold glass panels 46, that shall be described in greater detail below. As shown in the drawings, one end of each of side walls 22, 24 is positioned against vertical wall 14 of the existing structure. The other ends of side walls 22, 24 are attached to front wall 28. In the embodiment shown, front wall 28 is generally U-shaped and defines an opening 52 that allows access to the area defined by enclosure 10. In the embodiment shown, opening 52 is rectangular in shape.

Figure 1:
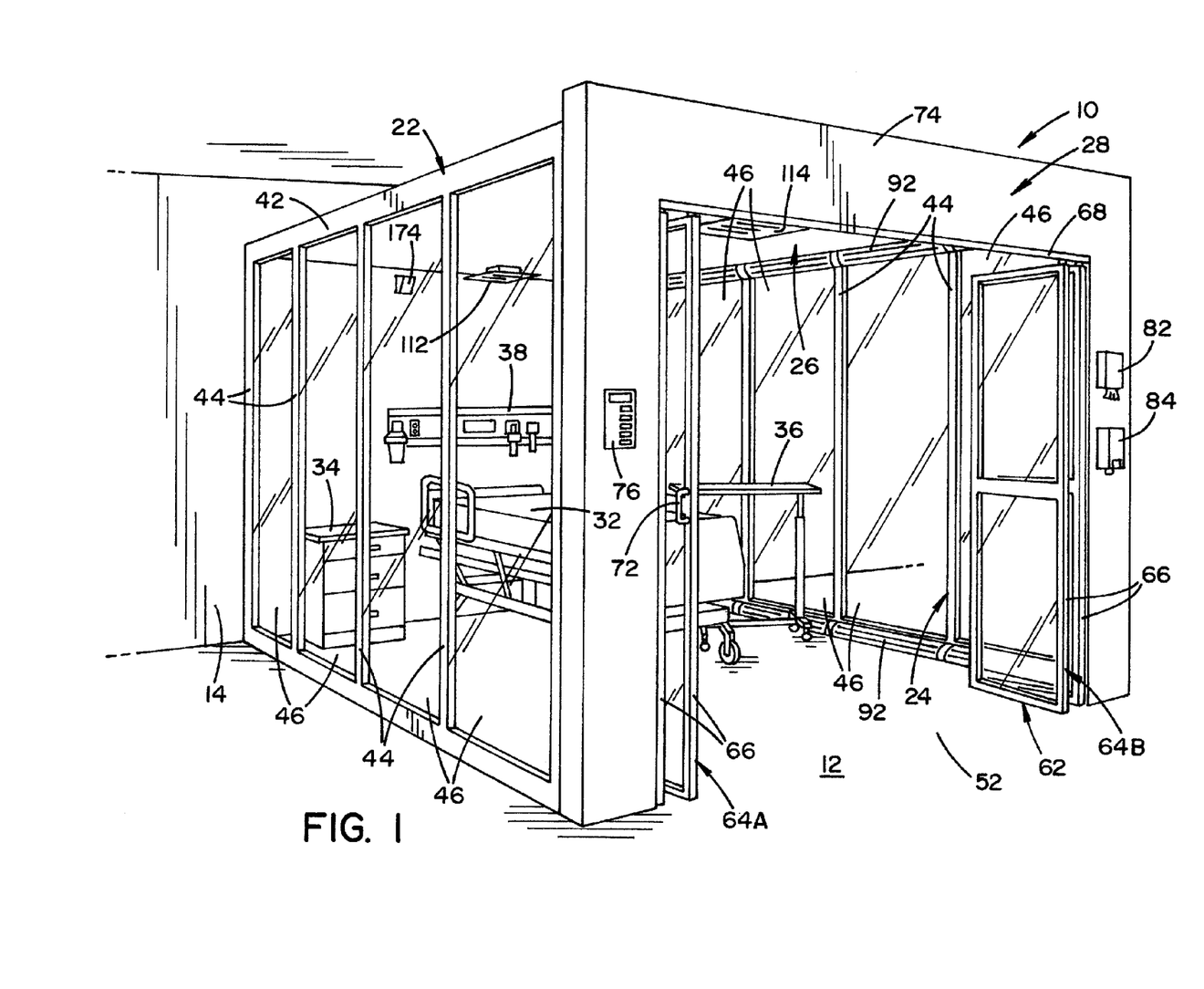
FIG. 1 is a perspective view showing a patient enclosure illustrating a preferred embodiment of the present invention.
Figure 2:
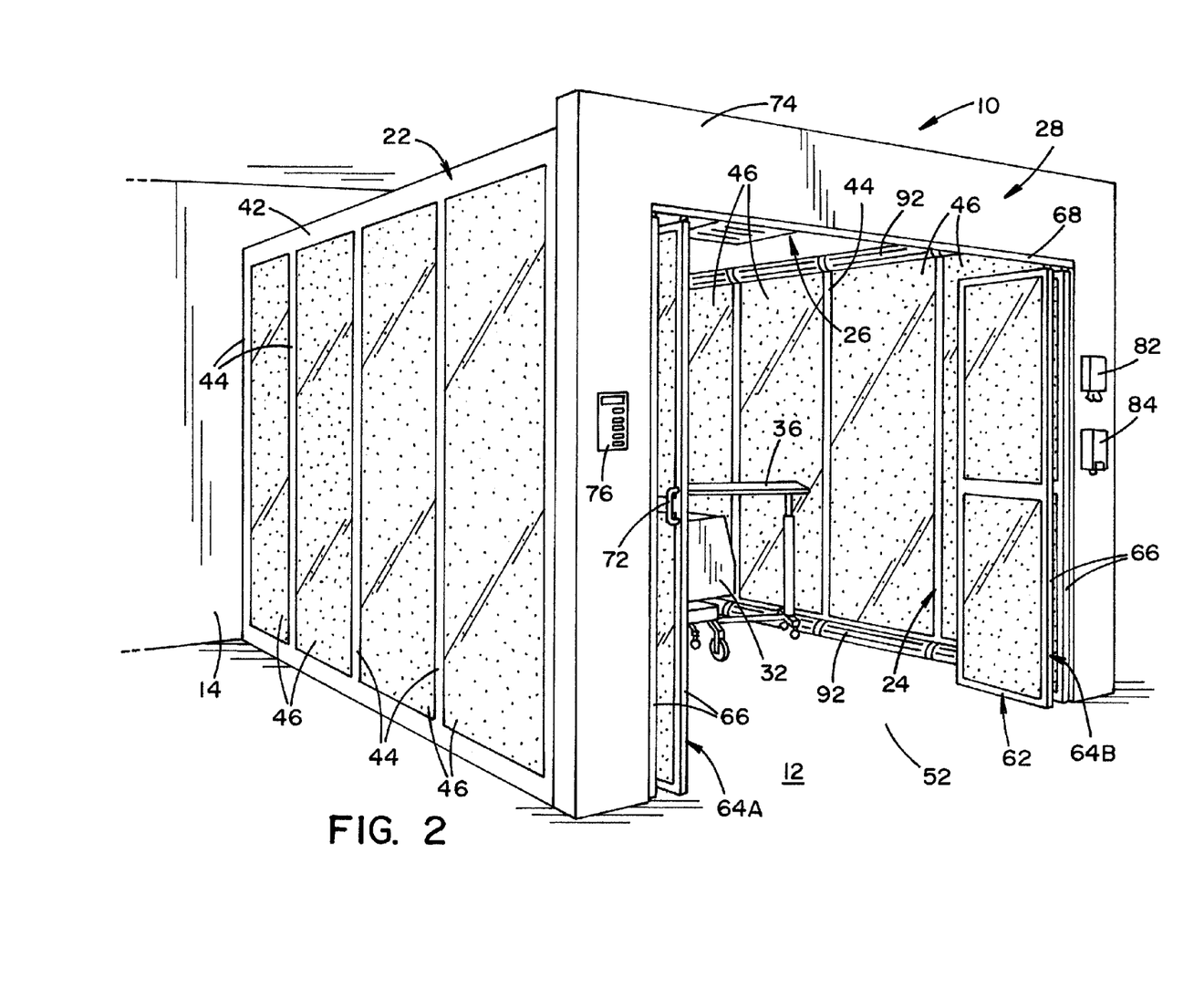
FIG. 2 is a perspective view of the enclosure shown in FIG. 1, wherein glass window panels of the enclosure are activated to make the panels opaque to light.
Figure 3:
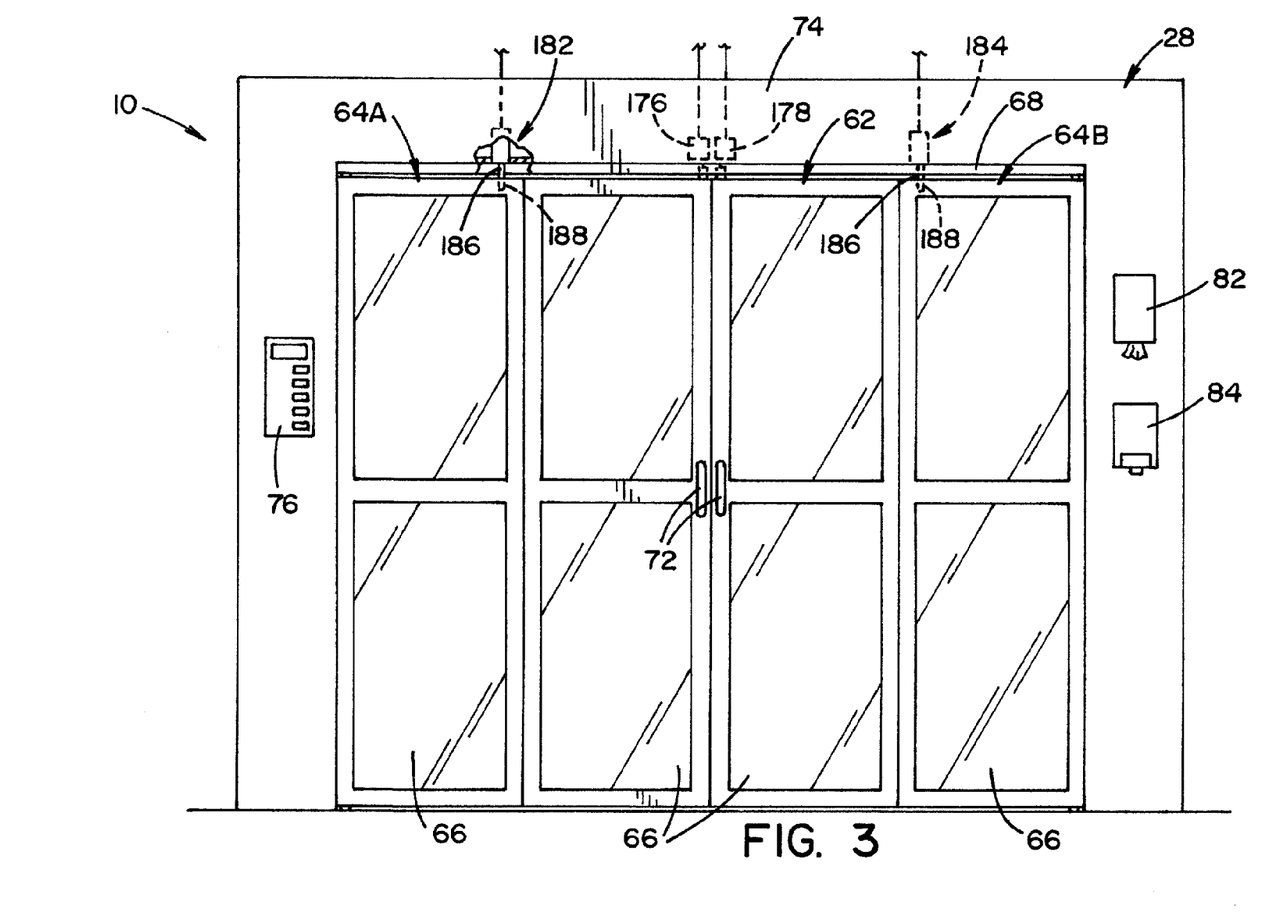
FIG. 3 is a front end view showing the entrance to the enclosure.
Figure 4:
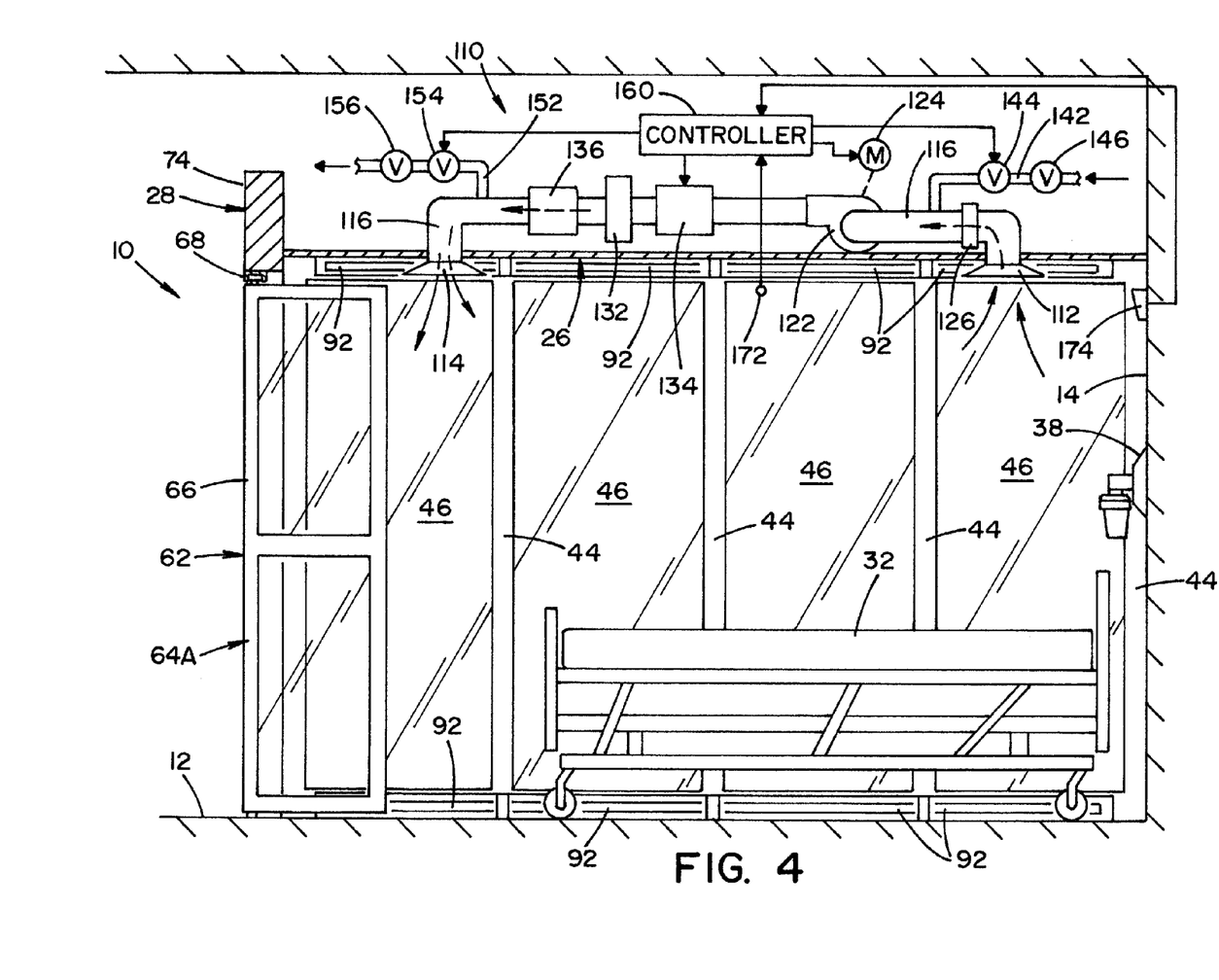
FIG. 4 is a cross sectional view of the enclosure showing an air circulation system for circulating air within the enclosure.

A door assembly 62 is provided within rectangular opening 52 of first wall 28. In the embodiment shown, door assembly 62 is comprised of two folding doors 64A, 64B. Each folding door 64A, 64B is comprised of a pair of side-by-side, rectangular panels 66. The vertical sides of door panels 66 are hinged. A horizontal track 68 is provided on front wall 28. The outer edges of the outermost door panels 66 are pinned to floor 12 and track 68 that extend along the lower edge of wall 28 to allow for pivotal rotation of the outermost door panels 66 about a vertical axis. The inner, upper corner of each of doors 64A, 64B is mounted to a roller that is confined within track 68 to allow doors 64A, 64B to fold within track 68. In this respect, each door 64A, 64B is movable between an open position, allowing access into the area defined by enclosure 10 (as best seen in FIG. 1) and a closed position, preventing access to the area defined by enclosure 10. A door handle 72 (as best seen in FIG. 3) is provided on the innermost panels 66 of each folding door 64A, 64B. As best seen in FIG. 4, front wall 28 is dimensioned to be taller, i.e., higher, than side walls 22, 24 to define a front facade 74 at the upper end of front wall 28. A control panel 76 is provided on front wall 28. A tissue or towel dispenser 82 and a hand-sanitizer dispenser 84 may also be provided on the front face of front wall 28.

The top wall 26 is joined to the upper edges of side walls 22, 24 and to front wall 28. Together with vertical wall 14 and floor 12 of the building, two spaced-apart side walls 22, 24, top wall 26, and front wall 28 basically define a patient care area, wherein a patient may be located.

In accordance with one aspect of the present invention, enclosure 10 is not air tight. In this respect, it is contemplated that cracks and/or gaps may exist between door assembly 62 and front wall 28, between door panels 66, between side walls 22, 24, top wall 26, and front wall 28, as well as between side walls 22, 24, top wall 26, and vertical wall 14 of the existing structure.

In accordance with another aspect of the present invention, a plurality of UV (ultra-violet) radiators 92 is disposed within the area defined by enclosure 10. In the embodiment shown, elongated, UV radiators are disposed along the upper and lower edges of frame 42 defining side walls 22, 24. More specifically, a plurality of aligned UV radiators is positioned in the corners where side walls 22, 24 meet top wall 26 and in the corner where side walls 22, 24 meet floor 12 of the building. UV radiators 92 are oriented to direct UV radiation into all regions of the space defined by enclosure 10. Preferably, UV radiators 92 are elongated, tubular lamps. In accordance with the present invention, each lamp produces UV-C radiation. UV-C radiation has a wavelength that ranges from 100 nm to 290 nm.

Referring now to FIG. 4, an air circulation system 110 for circulating air through the area defined by enclosure 10 is best seen. In the embodiment shown, air circulation system 110 is mounted to top wall 26 of enclosure 10. Air circulation system 110 is disposed above top wall 26 of enclosure 10 and has an air inlet 112 that extends through top wall 26 to communicate with the area defined by enclosure 10. In the embodiment shown, air inlet 112 is disposed near the back of enclosure 10, where enclosure 10 connects to vertical wall 14 of the existing building. An air outlet 114 extends through top wall 26 to communicate with the area within enclosure 10. Air outlet 114 is disposed near front wall 28 of enclosure 10. A conduit 116 connects air inlet 112 to air outlet 114. A blower 122 is disposed within conduit 116. Blower 122 is driven by a motor 124 that is schematically illustrated in the drawings. Blower 122 is oriented to circulate air through enclosure 10 by drawing air from enclosure 10 into the air inlet 112 and blowing the air through conduit 116 to air outlet 114. In other words, air inlet 112 is upstream, and air outlet 114 is downstream of blower 122 in the direction of air flow through conduit 116. A coarse filter 126 is disposed in conduit 116 between air inlet 112 and blower 122. Coarse filter 126 is dimensioned to remove gross matter, flowing with the air through conduit 116. In this respect, coarse filter 126 is dimensioned to remove particles down to one (1) micron. A HEPA filter 132 is disposed between blower 122 and air outlet 114. In other words, HEPA filter 132 is downstream from blower 122 in the direction of air flow. Preceding the HEPA filter is a plasma generator 134. Plasma generator 134 is dimensioned to generate oxidative species. Plasma generator 134 is disposed upstream of HEPA filter 132 such that the highly charged material exiting plasma generator 134 is captured by the electrically active media of HEPA filter 132. Organic materials trapped by the filter media (not shown) of HEPA filter 132 are continuously exposed to the plasma ions, thus resulting in complete biological decontamination of any organisms within the airstream within conduit 116. A catalytic converter 136 is disposed downstream of HEPA filter 132. Catalytic converter 136 destroys any ozone within the airstream before allowing the air to flow into enclosure 10. Coarse filter 126, HEPA filter 132, plasma generator 134 and catalytic converter 136 define an air filtration system that forms part of air circulation system 110.

In the embodiment shown, a supplemental air line 142 is connected to conduit 116 between blower 122 and coarse filter 126. A control valve 144 is disposed within supplemental air line 142 to control flow therethrough. A trim valve 146 is disposed within supplemental air line 142. Trim valve 146 is operable to adjust the internal pressure within supplemental air line 142 to a desired predetermined value. When valve 144 is in an open position, external air from the region or environment outside of enclosure 10 is allowed into conduit 116 upstream of blower 122.

Similarly, an air exhaust line 152 is connected to conduit 116 downstream of catalytic converter 136. A control valve 154 is disposed within air exhaust line 152 to control air flow therethrough. A trim valve 156 is also provided within air exhaust line 152. When valve 154 is in an open position, a portion of the air blown through conduit 116 by blower 122 is allowed to be vented from conduit 116 to the exterior of enclosure 10. As schematically illustrated in FIG. 4, a controller 160 is provided to control the operation of blower motor 124, valve 144 in supplemental air line 142, valve 154 in exhaust air line 152, and plasma generator 134. A pressure sensor 172 is provided within enclosure 10 to detect the pressure within enclosure 10.

A sensor 174 is also provided within enclosure 10 to detect the presence of a living being within enclosure 10. Sensor 172 can be an infrared sensor or a motion detector. Signals from pressure sensor 172 and sensor 174 are provided to controller 160.

A pair of proximity sensors 176, 178, shown in dotted lines in FIG. 3, is provided within front wall 28 to detect when folding doors 64A, 64B are in a closed position. Proximity sensors 176, 178 are connected to controller 160 to provide an indication of when doors 64A, 64B are in a closed position. Door-locking assemblies 182, 184 are provided to lock doors 64A, 64B in a closed position, as shall be described in greater detail below. In the embodiment shown, each door locking assembly is comprised of a retractable pin 186, as schematically illustrated in FIG. 3. Pin 186 is dimensioned to extend downwardly into a hole 188 in one door panel 66 of a folding door 64A, 64B to prevent opening door 64A, 64B when pin 186 is in the downward, locked position. In the embodiment shown, pin 186 is solenoid-actuated for reciprocal movement into an operative engagement of hole 188 in door panel 66. Each locking mechanism 182, 184 is connected to controller 160 which controls the operation thereof.

Referring now to the operation of enclosure 10, controller 160 is programmed to control the operation of air circulation system 110 and plasma generator 134. In this respect, controller 160 is also programmed to operate in several different modes of operation. More specifically, controller 160 is programmed to operate air circulation system 110 in one mode of operation to establish a negative pressure environment within enclosure 10 relative to the surrounding environment outside enclosure 10. In another mode of operation, controller 160 is operable to control air circulation system 110 to establish a positive pressure environment within enclosure 10 as compared to the environment outside enclosure 10. Still further, controller 160 is operable to run a decontamination routine to decontaminate surfaces within enclosure 10 once a patient has been removed from enclosure 10.

Referring to the operation of air circulation system 110, controller 160 controls motor 124 and blower 122 to continuously circulate air from the area within enclosure 10 through the air filtration system, i.e., coarse filter 126, HEPA filter 132, plasma generator 134 and catalytic converter 136 and back into enclosure 10. As illustrated in FIG. 4, when blower motor 124 is energized by controller 160, air is drawn from enclosure 10 into conduit 116 through air inlet 112. The circulating air passes first through coarse filter 126 which filters gross particles, i.e., particles having a particle size greater than one (1) micron from the air. The air is then directed through plasma generator 134 where an electric field generates oxidative species within the airstream. In other words, plasma generator 134 charges particles within the air. The air then passes through HEPA filter 132 that filters the air and removes microscopic particles and organisms from the airstream. The existence of the plasma ions within the airstream results in biological decontamination of the air and decontamination of HEPA filter 132 as the plasma ions flow with the air through HEPA filter 132. Plasma ions exiting past HEPA filter 132 are destroyed in catalytic converter 136 which removes any ozone such that only clean, filtered air is returned to enclosure 10 through air outlet 114, as illustrated by the arrows in FIG. 4. Basically, air circulation system 110 and the air filtration system operate continuously, as long as a patient is within enclosure 10.

In some instances, it is highly desirable to isolate a patient within enclosure 10 from the environment outside enclosure 10. In this situation, controller 160 would cause blower 122 and valve 144 on supplemental air line 142 and valve 154 on exhaust air line 152 to operate such that a positive pressure environment exists within enclosure 10, as compared to the environment outside enclosure 10. In this respect, controller 160 causes motor 124 to increase speed which increases air flow through blower 122. Controller 160 also causes valve 144 on supplemental air line 142 to open to allow additional air to be pulled into conduit 116 as a result of the operation of blower 122. Valve 154 on exhaust air line 152 would be moved to a closed position, such that the additional air that is brought into conduit 116 creates a higher pressure within enclosure 10 as a result of controller 160 causing blower 122 to increase speed.

As indicated above, enclosure 10 is not air tight, and cracks, voids, and gaps would exist between door assembly 62 and front wall 28. In addition, other cracks and voids may exist between side walls 22, 24 and vertical wall 14 and floor 12 of the existing structure. By maintaining a slightly higher pressure within enclosure 10, a constant flow of air through the voids, cracks, and gaps would be maintained, thereby insuring that no air from the external environment is brought into enclosure 10. By continuously maintaining a higher pressure within enclosure 10 as compared to outside enclosure 10, a flow of air through the aforementioned gaps, voids, and cracks is always maintained thereby insuring that no external air (which may be contaminated or contain undesirable bacteria) is allowed into enclosure 10 and the area around the patient.

In another situation, it may be desirable to insure that the environment within enclosure 10 is not allowed to escape outside enclosure 10. In this situation, controller 160 can operate to maintain a negative pressure environment within enclosure 10, wherein the pressure within enclosure 10 is always slightly below the pressure of the environment outside enclosure 10. In this mode of operation, valve 144 in supplemental air line 142 would be closed to prevent external air from being drawn into air circulation system 110.

Valve 154 in exhaust air line 152 would be opened to allow air in conduit 116 to bleed out of air circulation system 110. The result of such operation is that some of the air circulated through air circulation system 110 is allowed to be bled off from conduit 116. As a result, a slightly negative pressure is established within enclosure 10. This negative pressure and loss of air flow would be made up by external air flowing through the aforementioned cracks, gaps, or openings mentioned above. By maintaining the operation in this fashion, small amounts of make-up air outside enclosure 10 would be drawn into enclosure 10 during this mode of operation, thereby insuring that none of the internal air is released outside enclosure 10. It should be pointed out that exhaust air line 152 is located downstream from HEPA filter 132, plasma generator 134 and catalytic converter 136 such that only clean filtered air is allowed to escape from enclosure 10 during this mode of operation.

Referring now to another mode of operation, controller 160 is programmed to perform an enclosure decontamination cycle. Once a patient has been removed from enclosure 10, it is highly desirable that enclosure 10 be decontaminated. In accordance with the present invention, doors 64A, 64B to enclosure 10 would be closed prior to initiation of the decontamination cycle. Proximity sensors 176, 178 provide an indication to controller 160 that doors 64A, 64B are in a closed position, so as to allow operation of the decontamination cycle. Controller 160 actuates door locking mechanisms 182, 184 to lock doors 64A, 64B in a closed position to prevent opening of doors 64A, 64B during the decontamination cycle. Signals from motion sensor 174 enable controller 160 to determine whether a living being is within enclosure 10 before a decontamination cycle is initiated. If so, controller 160 would cease operation of the decontamination cycle and provide a warning signal on control panel 76. If no living being is detected within enclosure 10, a decontamination cycle is stared. Controller 160 causes the electrochromic glass panels 46 to turn to a reflective (inward to room) non-transparent state. Controller 160 then causes UV radiators 92 within the room to illuminate, thereby exposing all surfaces within enclosure 10 to high-intensity UV-C radiation. The reflective walls enhance the UV radiation exposure to all surfaces within the room.

After a pre-determined period of time need to sanitize the interior of enclosure 10, UV radiators 92 are deactivated and glass panels 46 are caused by controller 160 to return to a clear, transparent state.

In this respect, preferably, each of glass panels 46 within side walls 22, 24 and within door panels 66 is comprised of electrochromic glass and is controlled by controller 160, so that the entire room can be darkened to prevent personnel and staff outside enclosure 10 from being exposed to the high-intensity UV radiation during a decontamination cycle.

In accordance with another mode of operation, a patient or hospital staff may control the clear or opaque state of glass panels 46 at any time while a patient is within enclosure 10, and at times when a decontamination cycle is not being run, so as to allow observation by medical staff during the day or to allow a patient to rest in darkness and isolation at any time he/she may desire.

The present invention, thus, provides a small enclosure 10 that can be assembled within an existing room or region of a facility which allows for isolation of patients from the surrounding environment. Enclosure 10 further allows for the patient within enclosure 10 to be isolated from the external environment in some situations or can protect and isolate the environment outside of enclosure 10 from contamination or the environment inside enclosure 10 based upon the operation of the air circulation system and air filtration system.

Figure 5:
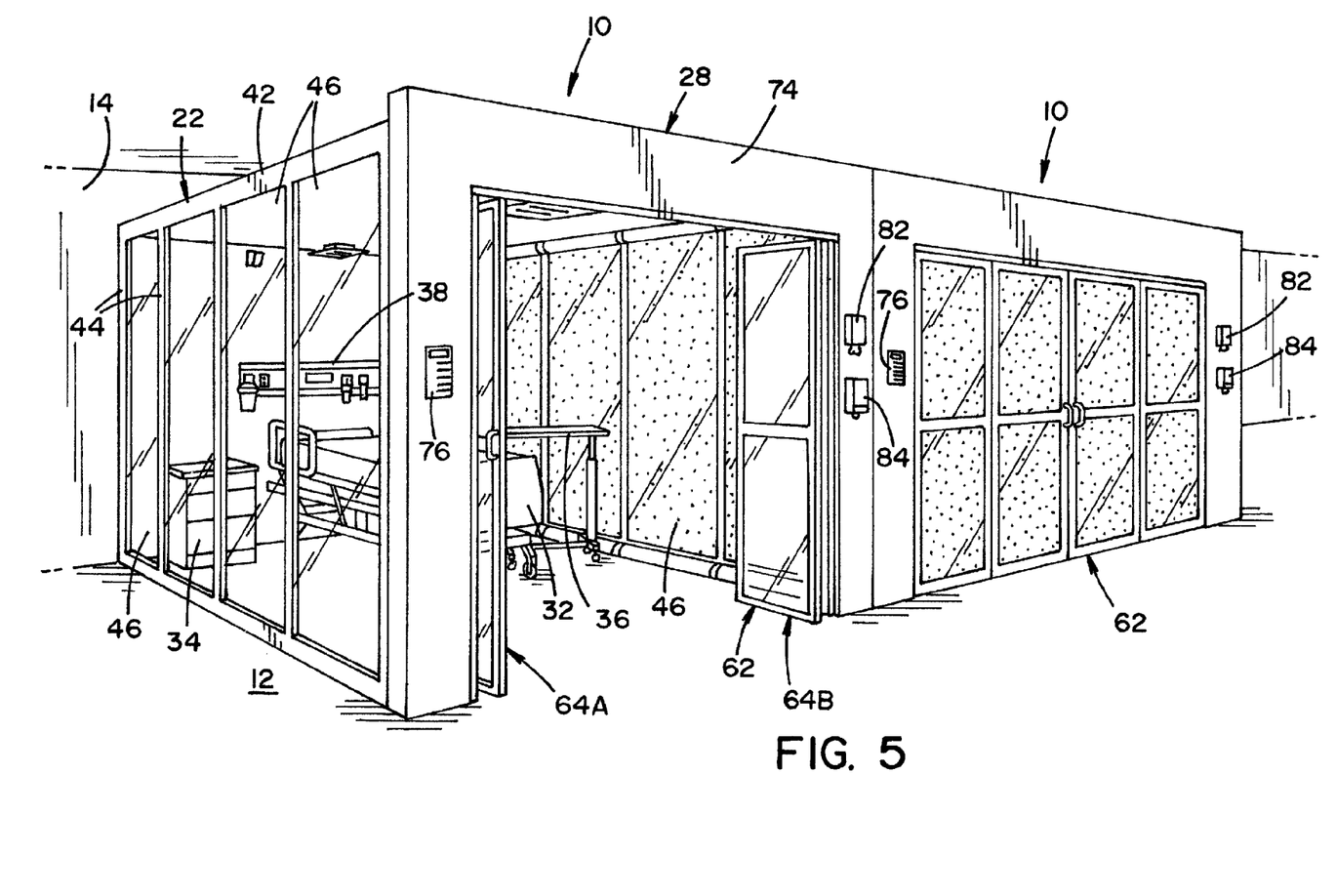
FIG. 5 is a perspective view showing one patient enclosure arranged alongside a second patient enclosure, wherein the window panels of the second patient enclosure are activated to make such window panels opaque to light.

FIG. 5 illustrates how multiple enclosures 10 may be arranged side-by-side within an existing room or structure to form separate isolated areas. Each enclosure 10 may be a free-standing structure as described above, or side-by-side enclosures 10 may be designed to have a common side wall therebetween.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A patient enclosure formed with a floor and a vertical wall of an existing structure, comprising:
   a plurality of enclosure walls, comprising:
      at least two spaced-apart side walls positioned on said floor and against said vertical wall;
      a top wall positioned on said side walls and against said vertical wall; and
      a front wall positioned against said side walls and said floor, said enclosure walls being dimensioned to define, along with said floor and said vertical wall, an enclosed area surrounding a location where a patient is positionable, at least one of said enclosure walls having a panel of electrochromic glass that is switchable between a clear state and an opaque state;
   a door assembly, comprising:
      an opening through said front wall allowing access into said enclosed area; and
      a door within said opening, said door movable between an open position allowing access, to said enclosed area and a closed position preventing access to said enclosed area;
   UV radiators positioned within said enclosed area;

an air circulation system for circulating air through said enclosed area, said air circulation system comprising:
a conduit having distal ends communicating with said enclosed area at spaced-apart locations therein;
a blower for blowing air through said enclosed area;
an air filtration system connected to said conduit such that air flowing through said conduit is filtered by said air filtration system;
an air inlet connecting said enclosed area with an environment surrounding said enclosed area, said air inlet having an inlet valve controlling air flow therethrough; and
an air outlet connecting said enclosed area with said environment surrounding said enclosed area, said air outlet having an outlet valve controlling air flow therethrough; and
a controller controlling said UV radiators, said blower, said inlet valve, and said outlet valve, said controller being programmed to create, within said enclosed area:
a positive pressure environment in which air from said enclosed area flows through one or more gaps to said environment surrounding said enclosed area; and
a negative pressure environment in which air from said environment surrounding said enclosed area is drawn into said enclosed area through said gaps, one or more of said gaps being formed between said door assembly and said front wall or between at least one of said enclosure walls and at least one of said vertical wall or another of said enclosure walls.

2. A patient enclosure as defined in claim 1, wherein said enclosure walls are dimensioned to be joined with said vertical wall and said floor to define said enclosed area.

3. A patient enclosure as defined in claim 1, wherein said UV radiators are disposed near said top wall.

4. A patient enclosure as defined in claim 1, wherein said UV radiators are disposed in a corner defined between at least one of said side walls and said top wall.

5. A patient enclosure as defined in claim 1, wherein each of said side walls comprises a plurality of glass panels, and
wherein each of said glass panels is formed of electrochromic glass that is switchable between one of a clear state, an opaque state, and a mirrored state.

6. A patient enclosure as defined in claim 1, wherein said air inlet is connected to said conduit on the upstream side of said blower.

7. A patient enclosure as defined in claim 1, wherein said air outlet is connected to said conduit on the downstream side of said blower.

8. A patient enclosure as defined in claim 1, wherein said circulation system is mounted on said top wall.

9. A patient enclosure as defined in claim 1, wherein said door includes at least one panel of electrochromic glass that is switchable between one of a clear state, an opaque state, and a mirrored state.

10. A patient enclosure as defined in claim 1, further comprising a sensor configured to sense a presence of a living being within said enclosed area.

11. A patient enclosure as defined in claim 1, wherein said air filtration system includes a HEPA filter and a plasma generator for generating oxidative species; said HEPA filter being exposed to said oxidative species.

12. A patient enclosure as defined in claim 11, further comprising a catalytic converter for destroying the oxidative species generated by said plasma generator.

13. A patient enclosure as defined in claim 1, wherein said gaps are formed between at least one of said enclosure walls and at least one of said vertical wall or another of said enclosure walls.

14. A patient enclosure as defined in claim 1, wherein at least one of said radiators is positioned in a corner defined by one of said side walls and said floor.

15. A patient enclosure as defined in claim 14, wherein another one of said radiators is positioned in a corner defined between at least one of said side walls and said top wall.

16. A patient enclosure as defined in claim 1, wherein each of said radiators essentially extends from one end of one of said side walls to another end of said side wall.

17. A patient enclosure as defined in claim 1, further comprising:
a door locking assembly configured to lock said door when said door is in said closed position, said assembly comprising a pin assembly positioned in said front wall and a recess corresponding with a position of said pin assembly formed in said door, the recess being dimensioned to receive a pin of said pin assembly, said pin assembly being configured to enable said pin to extend into said recess when said door is in said closed position.

18. A patient enclosure as defined in claim 17, further comprising:
a sensor configured to detect when said door is in said closed position and provide an indication to said controller that said door is in said closed position,
wherein, when said indication is provided to said controller, said controller instructs said pin assembly to enable said pin to extend.

* * * * *